United States Patent [19]

Gagnebien et al.

[11] Patent Number: 5,219,561
[45] Date of Patent: * Jun. 15, 1993

[54] COSMETIC COMPOSITION IN THE FORM OF A COMPACTED POWDER CONTAINING HOLLOW MICROSPHERES OF A THERMOPLASTIC SYNTHETIC MATERIAL

[75] Inventors: Didier Gagnebien, Levallois-Perret; Beatrice Defossez, Paris, both of France

[73] Assignee: L'Oreal, Paris, France

[*] Notice: The portion of the term of this patent subsequent to Apr. 27, 2010 has been disclaimed.

[21] Appl. No.: 660,991

[22] Filed: Feb. 27, 1991

[30] Foreign Application Priority Data

Feb. 28, 1990 [FR] France ............................... 90 02509

[51] Int. Cl.$^5$ ............................................. A61K 7/035
[52] U.S. Cl. ......................................... 424/69; 424/63; 424/401
[58] Field of Search ............................ 424/63, 69, 401; 524/513

[56] References Cited

U.S. PATENT DOCUMENTS

| | | | |
|---|---|---|---|
| 4,983,663 | 1/1991 | Orikasa et al. | 524/513 |
| 4,944,937 | 7/1990 | McCall | 424/60 |
| 4,994,264 | 2/1991 | Verdon et al. | 424/63 |
| 5,035,885 | 7/1991 | Arraudeau et al. | 424/69 |

FOREIGN PATENT DOCUMENTS

| | | |
|---|---|---|
| 0135060 | 3/1985 | European Pat. Off. . |
| 0254612 | 1/1988 | European Pat. Off. . |

OTHER PUBLICATIONS

S.T.N. Serveur De Bases De Donnees, Fichier Chemical Abstracts, vol. 109, No. 18, Abstract No. 155980, & JP-A-63 119 411.
Chemical Abstracts, vol. 104, No. 4, Jan. 1986, p. 290, No. 24076w.
French Search Report of FR 90 02509.

*Primary Examiner*—Thurman N. Page
*Assistant Examiner*—D. Colucci
*Attorney, Agent, or Firm*—Cushman, Darby & Cushman

[57] ABSTRACT

A cosmetic composition in the form of a compacted powder contains charges or pigments, or both, and hollow microspheres of a thermoplastic synthetic material having a specific mass ranging from 0.01 to 0.1 g/cm$^3$ and having a size less than 30 μm, the composition being free of acyl lysine.

8 Claims, No Drawings

COSMETIC COMPOSITION IN THE FORM OF A COMPACTED POWDER CONTAINING HOLLOW MICROSPHERES OF A THERMOPLASTIC SYNTHETIC MATERIAL

The present invention relates to the use, in the preparation of a compacted powder for makeup or the care of the body or face, a thermoplastic synthetic material in the form of hollow microspheres of fixed size, as well as to compositions in the form of a compacted powder containing such a material.

The use of hollow microspheres of a thermoplastic synthetic material in free non-compacted powders for make-up and the care of the skin has already been described; see French patent No. 86 09289 (publication No. 2 600 532).

However, it was not possible to obtain compacted powders of a satisfactory quality with microspheres having a diameter of 40–60 μm which were used in practice in the said French patent mentioned above, because of their much too great elasticity.

In effect, compacted powders must exhibit particular hardness characteristics. Hardness is a function of the applied compacting pressure. If the compacted product is too soft, it will be very fragile, and a much too significant amount of product will be removed at the time of use. On the other hand, if it is too hard, removal will be difficult.

Using hollow microspheres having a diameter of 40–60 μm, compression tests show that the compression was followed by a relaxation phenomenon which caused the appearance of fragmentation and cracks in the compacted product.

Moreover, a compacted product must exhibit a perfectly planar surface. Finally, the product must respond favorably to a drop test, that is to say, exhibit a restricted weight loss after being dropped under precise conditions.

These characteristics were not satisfactory using hollow microspheres having a diameter of 40–60 μm.

It has now been discovered that by using this type of thermoplastic synthetic material in the form of hollow microspheres having an average diameter less than 30 microns, it is possible to obtain compacted powders having quite satisfactory hardness characteristics and whose appearance is acceptable and whose production is easy.

The present invention thus relates to the use, in the preparation of a cosmetic composition in the form of a compacted powder, hollow microspheres of a thermoplastic synthetic material having a specific mass lower than 0.1 $g/cm^3$, the said hollow microspheres having a size lower than 30 μm and the said composition being free of acyl lysine.

The hollow microspheres are prepared in accordance with known procedures, such as those described in U.S. Pat. No. 3,615,972 and European patent application No. 0 056 219.

The hollow portion of the microspheres contain a gas such as a hydrocarbon (butane, pentane) air or any other conventionally employed gas.

The microspheres can be produced from any non-toxic and non-irritating thermoplastic material. These materials can be, for example, polymers or copolymers of ethylenic derivatives (for example, polyethylene, polystyrene, vinyl chloride/ arcylonitrile copolymer, etc.), polyamides, polyesters, urea-formaldehyde polymers, vinylidene chloride copolymers (for example, vinylidene chloride/acrylonitrile) etc.

Their size must be less than 30 μm and is preferably in the order of about 10 to 20 μm.

The specific mass of the hollow microspheres is, preferably, in the order of 0.01 to 0.1 $g/cm^3$.

The weight amount of the hollow microspheres in the compacted powders generally varies from 0.02 to 5 percent and preferably form 0.05 to 2 percent, based on the total weight of the composition.

The hollow microspheres useful in the composition of the present invention are principally those which are mentioned in the experimental portion given below.

The composition in the form of a compacted powder containing the thus defined microspheres also contains pigments and/or charges or fillers.

Preferably, they also contain an oily phase.

The pigments and/or charges are those conventionally employed in cosmetic compositions in the form of compacted powders. The pigments are selected principally from mineral pigments, organic pigments and nacreous pigments.

Representative mineral pigments include for instance:

titanium dioxide (rutile or anatase), optionally surface treated and listed in the Color Index under the reference CI 77891;

black, yellow, red and brown iron oxides listed under the CI references 77499, 77492, 77491;

manganese violet (CI 77742);

ultramarine blue (CI 77007);

chromium oxide (CI 77288);

hydrated chromium oxide (CI 77289); and ferric blue (CI 77510).

Representative organic pigments include in particular the following:

D&C Red No. 19 (CI 45170);
D&C Red No. 9 (CI 15585);
D&C Red No. 21 (CI 45380);
D&C Orange No. 4 (CI 15510);
D&C Orange No. 5 (CI 45370);
D&C Red No. 27 (CI 45410);
D&C Red No. 13 (CI 15630);
D&C Red No. 7 (CI 15850:1);
D&C Red No. 6 (CI 15850:2);
D&C Yellow No. 5 (CI 19140);
D&C Red No. 36 (CI 12085);
D&C Orange No. 10 (CI 45425);
D&C Yellow No. 6 (CI 15985);
D&C Red No. 30 (CI 73360);
D&C Red No. 3 (CI 45430);
Carbon black (CI 77266); and
Carmine lakes (CI 75470).

The nacreous pigments can be selected principally from: white nacreous pigments, such as mica coated with titanium oxide, bismuth oxychloride; and colored nacreous pigments, such as titanium mica with iron oxides, titanium mica with ferric blue or chromium oxide, titanium mica with an organic pigment of the type mentioned above, as well as those based on bismuth oxychloride.

These pigments can represent up to 70 percent of the total weight of the composition.

The charges or fillers are selected principally from: talc, which is a hydrated magnesium silicate, employed in particulate form generally having a size less than 40 μm; the said talc having humidity absorbing characteristics and being employed especially because of its unctuous touch or feel;

micas, which are alumino silicates of varying compositions, which are provided in the form of flakes having a size ranging from 2 to 200 μm, preferably 5 to 70 μm and a thickness of 0.1 to 5 μm, preferably 0.2 to 3 μm. The micas can be of natural origin (for example, muscovite, margarite, roscoelithe, lipidolithe, biotite) or of synthetic origin. The micas are generally transparent and impart to the skin a satiny appearance;

starch, and in particular, rice starch;

kaolin, which is a hydrated aluminum silicate, which is provided in form of particles having an isotropic form and having a size generally less than 30 μm and possessing good fatty body absorption properties;

zinc and titanium oxides, generally employed in the form of particles having a size not exceeding a few micrometers (or even less than 1 μm in the case of titanium oxide); these oxides have an unctuous feel, have a good covering powder and have a significant opacity;

precipitated calcium carbonate which, in the form of particles having a size less than 10 μm, has an unctuous feel or touch and permits to obtain a mat appearance;

magnesium carbonate or hydrocarbonate, which possesses principally properties of perfume fixation;

metallic soaps derived from organic carboxylic acids having 8 to 22 carbon atoms, preferably 12 to 18 carbon atoms, for example, zinc, magnesium or lithium stearate, zinc laurate, magnesium myristate, etc. These soaps, present generally in the form of particles having a size less than 10 μm, have an unctuous feel and facilitate adherence of the powder to the skin;

synthetic polymer powders, such as polyethylene, polyesters (for example polyethylene isophthalate or terephthalate) and polyamides (for example, nylon), in the form of particles having a size less than 50 μm, which possess absorbing properties and impart to the skin a velvety appearance.

These charges can represent up to 95% of the total weight of the composition.

The pigments and charges can be coated by substances such as amine acids, silicones, metallic salts or collagen, principally in order to modify their surface state.

The oily phase is constituted by at least one fatty body, liquid or solid at ambient temperature, and/or by an oleosoluble synthetic polymer whose use in cosmetics is known.

Representative fatty bodies liquid at ambient temperature include mineral, animal, vegetable or synthetic oils, or even silicone oils or liquid waxes. Specific examples of oils are the following: petrolatum oil, liquid lanolin, arara oil, sesame oil, macadamia oil, jojoba oil and synthetic triglycerides.

Representative oleosoluble synthetic polymers include polyvinylpyrrolidone/hexadecene or PVP/eicosene copolymers, such as the products sold by GAF Corp. under the tradenames "GANEX V-216" and "GANEX V-220".

The optionally added oily phase represents from 0 to 25 percent of the total weight of the composition, and preferably 3 to 20 percent.

Other various ingredients can be introduced into the compositions to be compacted, such as antiseptics (trichlorodiphenyl ether), cationic agents, boric acid, etc...) which are employed principally in deodorizing powders for the body or the feet and in baby powders; astringent agents, which are employed in deodorizing powders or in foot powders, such as aluminum hydroxychloride or alums; sunscreen agents; softening agents; hydrating agents (sorbitol, glycerine); cicatrisive agents; anti-free radical agents; vitamins; perfumes; etc.

These ingredients can represent up to 5 percent of the total weight of the composition.

Finally, the compacted powders, in accordance with the present invention, optionally contain hydrosoluble stability agents (up to 20 weight percent of an aqueous solution), such as natural or synthetic gums, cellulose derivatives or acrylic polymers.

The powders of the present invention are prepared in accordance with conventional techniques for the preparation of compacted powders. Generally the following procedures are carried out:

The pigments and/or charges, as well as the powdery additives optionally present, are admixed with the hollow microspheres.

The oily phase and/or the stability agents, as well as the other optional ingredients are added, and the whole is mixed together.

The resulting mixture is then compacted using a conventional press or automatic compaction in metallic pans.

Comparative Test

Studies of the development of the hardness of compacted powders, as a function of the compacting pressure, have been carried out. These studies have compared several powders containing microspheres of different granulometries, and also different amounts of oils. The microspheres employed are products marketed under the tradenames "EXPANCEL 551 DE (40 μm), 551 DE 20 (20 μm) and 551 DE 12 (12 μm) by Kemanord Plast.

The following compositions were studied (Table I).

TABLE I

| Formulas | 1 | 2 | 3 | 1' | 2' |
|---|---|---|---|---|---|
| Chromium oxide | 15 | 15 | 15 | 15 | 15 |
| Titanium mica | 35 | 35 | 35 | 35 | 35 |
| Talc | 40.8 | 40.8 | 40.8 | 29.5 | 29.5 |
| Petrolatum oil | 5.4 | 5.4 | 5.4 | 20 | 20 |
| Lanolin | 0.5 | 0.5 | 0.5 | — | — |
| Oleic alcohol | 1 | 1 | 1 | — | — |
| Petrolatum | 1 | 1 | 1 | — | — |
| Isopropyl myristate | 0.8 | 0.8 | 0.8 | — | — |
| Propyl parahydroxybenzoate | 0.2 | 0.2 | 0.2 | 0.2 | 0.2 |
| Expancel 551 DE | 0.3 | — | — | 0.3 | — |
| Expancel 551 DE 20 | — | 0.3 | — | — | 0.3 |
| Expancel 551 DE 12 | — | — | 0.3 | — | — |

Results

Hardness: It is measured by indentation using a "ZWICK" durometer, Reference 3114. For this type of composition, the optimum hardness is situated at about 40° Shore A. This hardness is reached for compacting pressures of about 70 bars for composition 2 and about 55 bars for composition 3. On the other hand, for composition 1, the hardness reaches 35° Shore A only for a compacting pressure of about 100 bars, and still does not reach 40° Shore A for a compacting pressure of 120 bars.

For composition 2', the hardness of 40° Shore A is reached composition 1', the hardness does not reach 35° Shore A for a compacting pressure of 100 bars.

Drop Test: This test consists in releasing the compacted powder twice from a height of 1 meter, then determining, by weight, the percentage of powder removed. In this test, the accepted norm is a weight loss less than 10%.

For compositions 2 and 3, the weight loss is less than 10% for compacting pressures greater than about 75 and 60 bars, respectively, and the weight loss becomes zero for compacting pressures greater than 80 bars. For composition 1, the weight loss remains greater than 30%, even for compacting pressures reaching 120 bars.

For composition 2', the weight loss is less than 10% for compacting pressures greater than about 55 bars, and becomes zero for compacting pressures greater than or equal to 80 bars. For composition 1', the weight loss is still greater than 20% for a compacting pressure of 100 bars.

Surface state: For a compacting pressure of 80 bars, the surface state of compositions 2 and 3 is satisfactory. For composition 1, the surface is not planar and losses of material are observed near the edges of the pan.

EXAMPLES

In the following examples, the compositions have been prepared in the previously described manner.

In these examples, the compositions are defined by the weight amount of the ingredients.

| Example 1 - Makeup Powder | |
|---|---|
| Titanium dioxide | 10 |
| Colored titanium mica | 30 |
| D&C Red No. 30 | 1.2 |
| Propyl parahydroxybenzoate | 0.2 |
| Petrolatum oil | 6 |
| Expancel 551 DE 12 | 0.8 |
| Hydroxymethoxybenzophenone, such as the product "UVINUL M40" sold by BASF | 0.5 |
| Talc, sufficient amount for | 100 |

This makeup is applied with a brush.

| Example 2 - Compacted Face Powder | |
|---|---|
| Polyethylene powder | 5 |
| Iron oxides | 6 |
| Titanium dioxide | 10 |
| Mica | 15 |
| Isopropyl myristate | 1.5 |
| Petrolatum oil | 1.5 |
| Expancel 551 DE 20 | 0.5 |
| Sorbitol | 0.5 |
| Talc, sufficient amount for | 100 |

This powder is applied using a powder puff or a brush.

| Example 3 - Compacted Face Powder | |
|---|---|
| Titanium dioxide | 10 |
| Rice starch | 15 |
| Iron oxides | 8 |
| Cyclomethicone | 5 |
| Propyl parahydroxybenzoate | 0.2 |
| Polyamide powder | 10 |
| Expancel 551 DE 12 | 1.5 |
| Vitamin E | 0.5 |
| Talc coated with silicones, sufficient amount for | 100 |

This powder is applied with a powder puff or a brush.

In the preceding formulation the cyclomethicone can be replaced by the same amount of polydimethylsiloxane.

| Example 4 - Compacted Perfumed Body Powder | |
|---|---|
| Iron oxide | 0.07 |
| Zinc stearate | 6 |
| Propyl parahydroxybenzoate | 0.2 |
| Expancel 551 DE 20 | 0.5 |
| Perfume | 4 |
| Talc, sufficient amount for | 100 |

This powder is applied with a powder puff or a brush.

| Example 5 - Wet or Dry Foundation Powder "Two way cake" | |
|---|---|
| Bismuth oxychloride | 15 |
| Starch | 10 |
| Iron oxides | 6 |
| Titanium dioxide | 7 |
| Petrolatum oil | 4 |
| Expancel 551 DE 12 | 1.2 |
| Gum arabic (30% aqueous solution) | 3 |
| Talc, sufficient amount for | 100 |

This foundation powder can be used either dry, i.e. using a powder puff or a brush, or wet using a moistened latex sponge.

| Example 6 - Eyelid Makeup Product | |
|---|---|
| Chromium oxide | 6 |
| Iron oxide | 7 |
| Polyamide powder | 15 |
| Cyclomethicone | 9 |
| Titanium mica | 30 |
| Expancel 551 DE 12 | 0.9 |
| Talc, sufficient amount for | 100 |

This eyelid makeup composition is applied with a foam or latex applicator or with a brush.

In the preceding formulation the cyclomethicone can be replaced by the same amount of hexadecyldimethicone.

| Example 7 - Compacted Face Powder | |
|---|---|
| Polyamide powder | 10 |
| Mica | 30 |
| Zinc stearate | 4 |
| Titanium dioxide | 2 |
| Polyvinylpyrrolidone/hexadecene copolymer, (GANEX V-216, sold by GAF) | 0.5 |
| Petrolatum oil | 5.5 |
| Iron oxide | 3 |
| Expancel 551 DE 20 | 0.3 |
| Talc, sufficient amount for | 100 |

This powder is applied with a powder puff or a brush.

We claim:

1. A cosmetic composition in the form of a compacted powder comprising a filler or a pigment or both present in an amount ranging up to 95 percent by weight based on the total weight of said composition and hollow microspheres of a non-toxic and non-irritating thermoplastic synthetic material having a specific mass ranging from 0.01 to 0.1 g/cm$^3$ and having a size less than 30 μm, said hollow microspheres being present in an amount ranging form 0.02 to 5 percent by weight based on the total weight of said composition and said composition being free of acyl lysine.

2. The cosmetic composition of claim 1 wherein said hollow microspheres have a size ranging from 10 to 20 μm.

3. The cosmetic composition of claim 1 wherein the thermoplastic synthetic material of said hollow microspheres is selected from a polymer or copolymer of an ethylenic hydrocarbon, a polyester, a polyamide, a urea-formaldehyde polymer or a vinylidene chloride copolymer.

4. The cosmetic composition of claim 1 wherein the thermoplastic synthetic material of said hollow microspheres is a vinylidene chloride/acrylonitrile copolymer.

5. The cosmetic composition of claim 1 wherein said hollow microspheres are present in an amount ranging from 0.05 to 2 percent by weight based on the total weight of said composition.

6. The composition of claim 1 wherein said pigment is present in an amount ranging up to 70 percent by weight based on the total weight of said composition.

7. The composition of claim 1 which also contains 0 to 25 percent by weight of a fatty phase based on the total weight of said composition.

8. A cosmetic composition in the form of a compacted powder comprising a filler or a pigment or both present in an amount ranging up to 95 percent by weight based on the total weight of said composition and hollow microspheres of a non-toxic and non-irritating thermoplastic synthetic material having a specific mass ranging from 0.01 to 0.1 g/cm$^3$ and having a size less than 30 μm, said hollow microspheres being present in an amount ranging from 0.02 to 5 percent by weight based on the total weight of said composition, said thermoplastic synthetic material being selected from the group consisting of an ethylenic hydrocarbon polymer or copolymer, a polyester, a polyamide, a urea-formaldehyde polymer and a vinylidene chloride copolymer, and said composition being free of acyl lysine.

* * * * *